United States Patent
Gross et al.

(10) Patent No.: US 6,700,001 B2
(45) Date of Patent: Mar. 2, 2004

(54) PROCESS FOR STEREOSELECTIVE SYNTHESIS OF 2-HYDROXYMETHYL CHROMANS

(75) Inventors: Jonathan L. Gross, Robbinsville, NJ (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 0 days.

(21) Appl. No.: 10/264,947

(22) Filed: Oct. 4, 2002

(65) Prior Publication Data
US 2003/0105342 A1 Jun. 5, 2003

Related U.S. Application Data
(60) Provisional application No. 60/327,400, filed on Oct. 5, 2001.

(51) Int. Cl.$^7$ ............................................. C07D 311/58
(52) U.S. Cl. ......................... 549/407; 549/389; 546/89
(58) Field of Search ................................. 549/407, 389; 546/89

(56) References Cited

U.S. PATENT DOCUMENTS

| 4,424,389 A | 1/1984 | Sakito |
| 5,318,988 A | 6/1994 | Schohe-Loop et al. |
| 5,371,094 A | 12/1994 | Heine et al. |

FOREIGN PATENT DOCUMENTS

| GB | 1 590 938 | 6/1981 |
| JP | 08238095 | 9/1996 |
| WO | WO 91/16322 A2 | 10/1991 |
| WO | WO 02/20507 A1 | 3/2002 |

OTHER PUBLICATIONS

U.S. patent application Ser. No. 10/264,528, Gross et al., Not Published.
Mitsunobu, Synthesis, 1–27 (1981).
Goujon et al., J. Chem. Soc., Perkin Trans., 1, 496–499 (2002).
Chang et al., J. Org. Chem., 63, 864–866 (1998).
Grubbs et al., Tetrahedron 54, 4413–4450 (1998).
Kolb et al., Chem. Rev., 94, 2483–2547 (1994).
Achinami Kazuo, Patent Abstracts of Japan, vol. 1997, No. 1.

*Primary Examiner*—Bernard Dentz
(74) *Attorney, Agent, or Firm*—Kimberly R. Hild

(57) ABSTRACT

A process for the stereoselective synthesis of 2-hydroxymethyl-chromans of formula (II) is provided

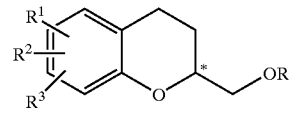

where R, $R^1$, $R^2$ and $R^3$ are as defined herein. The compound of formula (II) is prepared using an optically active benzene compound of formula (I)

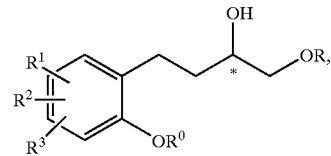

where $R^0$ is as defined herein. The 2-hydroxymethyl-chroman compounds of formula (II) are useful as intermediates for preparing a variety of medicinal agents.

16 Claims, No Drawings

PROCESS FOR STEREOSELECTIVE SYNTHESIS OF 2-HYDROXYMETHYL CHROMANS

CROSS REFERENCE TO RELATED APPLICATIONS

This application claims the benefit under 35 U.S.C. §119 (e) to U.S. provisional application Ser. No. 60/327,400 filed Oct. 5, 2001, which is hereby incorporated by reference in its entirety.

FIELD OF THE INVENTION

The present invention relates to a process for the stereoselective preparation of 2-hydroxymethyl-chromans.

BACKGROUND OF THE INVENTION

Various 2-yl chroman derivatives have been used as intermediates in the synthesis of various agents such as medicinal agents. For example, U.S. Pat. No. 5,371,094 discloses the use of 2-yl methyl chroman derivatives in the preparation of a series of azaheterocyclylmethyl-chromans that are useful for controlling diseases of the central nervous system. Also, for example, U.S. Pat. No. 5,318,988 discloses the use of 2-yl chroman derivatives of the formulae:

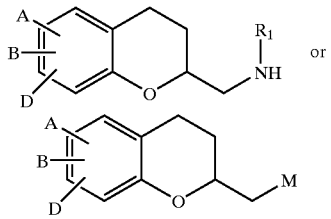

for preparing compounds having the formula

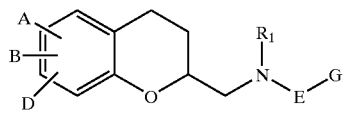

where M represents a typical leaving group such as chloride, bromide, iodide, tosylate, mesylate or triflate, E represents a direct bond or an alkylene or alkenylene having in each case up to 10 carbon atoms, which are optionally substituted by phenyl, G represents an optionally substituted cyclic or heterocyclic moiety containing one or more rings. These compounds are disclosed as being useful for combating disease of the central nervous system.

The processes disclosed in these patents for making chroman derivatives are nonstereoselective necessitating separation of the diastereomers into their single stereoisomeric constituents through conventional methods. It would be desirable to provide processes for the efficient production of 2-yl chroman derivatives that are stereoselective.

Processes for making 2-yl chroman derivatives in a non-stereoselective manner are known. For example, Ellis, G. P., in Heterocyclic Compounds, Vol. 31, chapter entitled "Chromenes, Chromenones, and Chromones", John Wiley & Sons, NY (1977), discloses examples of such nonstereoselective processes.

It would be desirable to provide a stereoselective process for producing 2-yl chroman derivatives.

SUMMARY OF THE INVENTION

The present invention provides a process for the stereoselective synthesis of 2-hydroxymethyl-chroman that includes:

(a) providing an optically active benzene compound of formula (I),

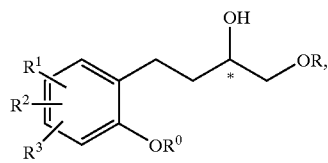

where $R^0$ is hydrogen or an oxygen protecting group,

R is an oxygen protecting group or hydrogen, or the moiety OR is a leaving group, and $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, a $C_2$ to $C_7$ alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents, where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms or any combination of i), ii) or ii);

(b) if $R^0$ is not H, deprotecting the $OR^0$ moiety of formula (I) to produce a phenol compound of formula (IA)

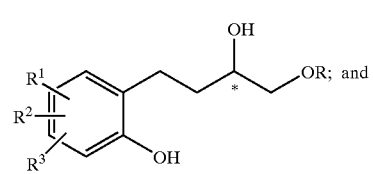

(c) reacting the phenol of formula (IA) in one or more reactions to form a 2-hydroxymethyl-chroman of formula (II)

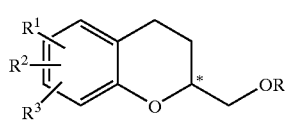

where at least one of the reactions is a stereospecific cyclization reaction.

In one embodiment, when R of formula (I) and (IA) is hydrogen, the 2-hydroxymethyl chroman is formed by one or more reactions that includes treating the phenol of formula (IA) with hydrogen bromide and acetic acid to produce a bromine compound of formula (2b)

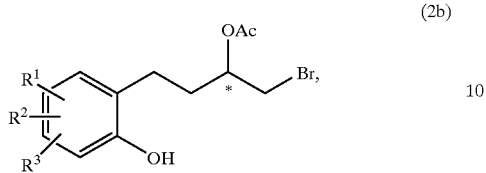

where Ac is an acyl group; and treating the bromine compound of formula (2b) with a base in a stereospecific cyclization reaction.

In another embodiment, when the R of formula (I) and (IA) is an oxygen protecting group or the moiety OR of formula (I) and (IA) is a leaving group, the 2-hydroxymethyl chroman is formed by a stereospecific cyclization reaction that includes treating the phenol of formula (IA) with triphenylphosphine and diethyl azodicarboxylate.

In yet another embodiment of the present invention, the compound of formula (I) is formed by a reaction that includes an osmium-catalyzed asymmetric dihydroxylation of a butene compound of formula (1e)

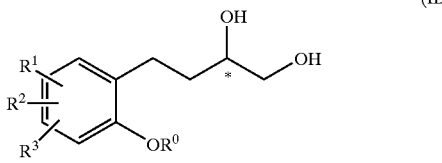

to produce a compound of formula (IB)

(IB)

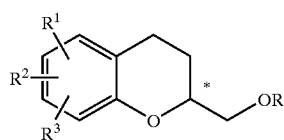

where $R^0$, $R^1$, $R^2$ and $R^3$ are defined as above.

DETAILED DESCRIPTION OF THE INVENTION

The present invention is directed to a stereoselective process for preparing 2-hydroxymethyl chromans of the following formula (II):

II

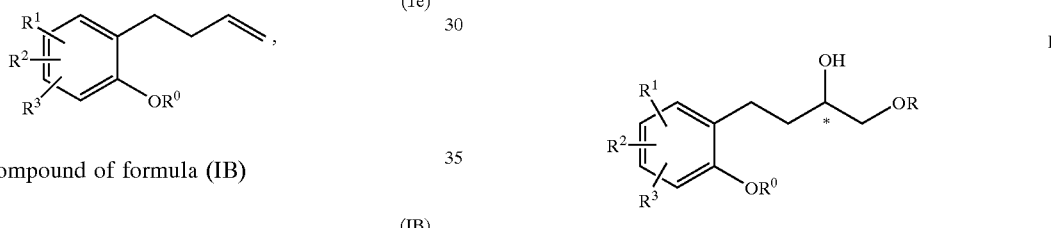

where:
R is an oxygen protecting group or hydrogen, or the moiety OR is a leaving group; and
$R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, a $C_2$ to $C_7$ alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group such as trifluoromethyl or trifluoromethoxy, an amino group or a mono- or di-alkylamino having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii) or iii).

The process of the present invention requires an optically active benzene compound of formula I as a starting material:

I

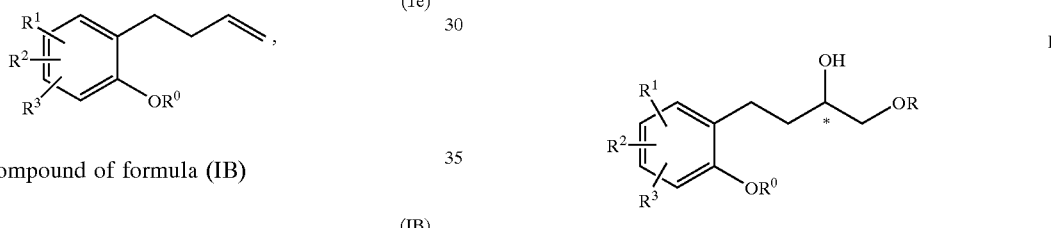

where $R^0$ is hydrogen or an oxygen protecting group, and R, $R^1$, $R^2$ and $R^3$ are defined as before. The benzene compound of formula I, or a derivative of this compound, as described in further detail hereinafter, is reacted in a stereospecific cyclization reaction to form the 2-hydroxymethyl chroman of formula (I).

By "stereoselective" as used herein, it is meant a reaction where one stereoisomer is preferentially formed over another. Preferably, the process of the present invention will produce a 2-hydroxymethyl-chroman having an enantiomer excess of at least about 30%, more preferably at least about 40%, and most preferably at least about 50%, where enantiomer excess is the mole percent excess of a single enantiomer over the racemate.

By "stereospecific" as used herein, it is meant a reaction where starting materials differing only in their spacial configuration are converted to stereoisomerically distinct products. For example, in a stereospecific reaction, if the starting material is enantiopure (100% enantiomer excess "ee"), the final product will also be enantiopure. Similarly, if the starting material has an enantiomer excess of 50%, the final product will also have a 50% enantiomer excess.

By "optically active" as used herein, it is meant a non-racemic mixture of chiral molecules. The "*" as used in the chemical formulas indicates the chiral carbon providing the optical activity.

As used herein, unless otherwise indicated, any moiety containing an alkyl or alkenyl group such as for example, an alkyl, alkane, alkenyl, alkoxy, carboalkoxy, or alkanamido group, may be branched or straight chained and contain up to 7 carbon atoms in the alkyl/alkenyl chain. Alkenyl groups, unless otherwise, indicated may be monounsaturated, polyunsaturated or fully unsaturated. Cycloalkyl means a carbocyclic ring having 3–8 carbon atoms. Aromatic and aryl mean an aromatic 5- to 7-membered carbocyclic ring such as phenyl. Heteroaromatic and heteroaryl mean an aromatic 5- to 7-membered ring having one or two heteroatoms which independently may be N, O, or S. Acyl means an alkanoyl group having 2 to 7 carbon atoms. Any moiety containing an alkyl, alkenyl, cycloalkyl aromatic, heteroaromatic, aryl, or heteroaryl group may optionally be substituted as defined hereinafter. For example, alkyl moieties may be halogenated, such as mono- or difluoromethyl or mono- or difluoromethoxy. Halogen means fluorine, chlorine, bromine or iodine.

The term "substituted" as used herein refers to a moiety, such as an aryl or alkyl moiety having from 1 to about 5 substituents, and more preferably from 1 to about 3 substituents independently selected from halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms. Preferred substituents are halogen atom, a cyano, nitro or hydroxyl group, a $C_1$–$C_6$ alkyl group, or a $C_1$–$C_6$ alkoxy group.

The term "oxygen protecting group" as used herein refers to any moiety that is used to protect an —OH moiety. Any moiety that is relatively inert to reaction conditions under which alcohols normally react, such as under Mitsunobu reaction conditions may be used. Examples of preferred oxygen protecting groups useful in the present invention include alkyl groups; aryl groups such as benzyl or 2-nitrobenzyl; or silyl groups such as t-butyldimethylsilyl or triethylsilyl to form the corresponding ether as the protected oxygen group. Also, the oxygen protecting group may be, for example, aryl or alkyl carbonyl moieties to form aryl or alkyl esters as the protected oxygen group, such as acetate or pivaloate. One skilled in the art will be able to identify other suitable oxygen protecting groups such as those described in T. W. Green and P. G. M. Wuts: *Protective Groups in Organic Synthesis*, Second Edition (Wiley, NY, 1991), the disclosure of which is hereby incorporated by reference in its entirety.

The term "leaving group" as used herein refers to any moiety or atom that is susceptible to nucleophilic substitution or elimination. Typically, these are atoms or moieties that when removed by nucleophilic substitution or elimination are stable in anionic form. Examples of leaving groups useful in the present invention include alkyl- or arylsulphonate groups such as tosylate, brosylate, mesylate or nosylate, or halides such as chloride, bromide, or iodide. In the case of a halide leaving group, the entire "OR" moiety is replaced with the halide. Tosylate, or 4-methylbenzenesulfonate, is an especially preferred leaving group in the practice of this invention.

The term "leaving group reagent" or "oxygen protecting group reagent" refers to a reactant used to protect or replace the hydroxyl moiety. For example, the reagent p-toluenesulfonyl chloride may be used to replace a hydroxyl moiety with a tosylate moiety. Also for example, the reagent benzyl bromide may be used to provide a benzyl ether protecting group.

The starting optically active benzene compound of formula (I) can be prepared by any method known to those skilled in the art as long as the resulting compound is optically active. Preferably, the optically active benzene compound of formula (I) provided in the process of the present invention will have an enantiomer excess of at least about 30%, more preferably at least about 40%, and most preferably at least about 50%.

A preferred method for preparing the benzene compound of formula (I) is illustrated in Scheme I, below.

SCHEME I

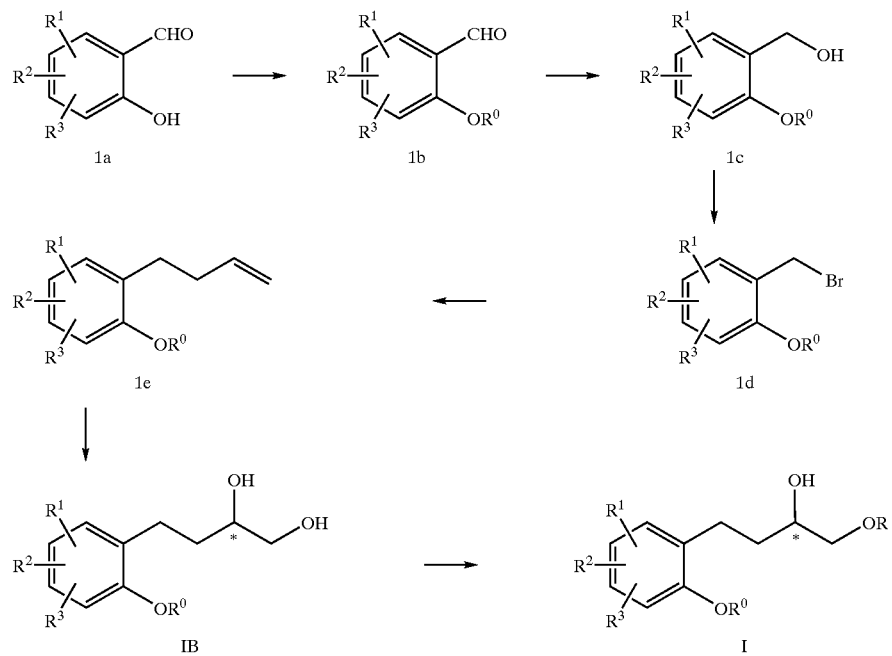

Referring to Scheme I, protection of the phenol present in the salicylaldehyde (1a) may be accomplished using any oxygen protecting reagent known to those skilled in the art. In a preferred embodiment, the salicylaldehyde is treated with the oxygen protecting reagent benzyl bromide in the presence of a base such as potassium carbonate to form the corresponding benzyl ether (1b). The aldehyde moiety on the benzyl ether (1b) is then converted, using any technique known to those skilled in the art, in one or more reactions into a butenyl moiety to form the 2-butenyl phenol derivative of (1e), where at least one of the reactions is an intermolecular allylation reaction. In a preferred embodiment, shown in Scheme I, the aldehyde moiety of the benzyl ether (1b) is reduced using any technique known to those skilled in the art to produce the benzyl alcohol of formula (1c). In a preferred embodiment, this reduction is carried out with sodium borohydride. The benzyl alcohol (1c) is then converted to a benzylbromide (1d) using techniques known to those skilled in the art. Preferably, this conversion is carried out using carbon tetrabromide and triphenylphosphine. The benzylbromide (1d) is then reacted with allyl magnesium bromide in an addition reaction to provide a 2-butenyl phenol derivative (1e). Alternatively, for example, the allylation reaction (not shown) could be carried out directly on the aldehyde moiety of compound (1b) followed by reduction of the resulting alcohol to form the 2-butenyl phenol derivative (1e). The butenyl group on the phenol derivative (1e) serves as the substrate for an asymmetric dihydroxylation step discussed further below.

As mentioned, the 2-butenyl phenol derivative (1e) is reacted in a catalyzed asymmetric dihydroxylation reaction to form an optically active butanediol of formula (IB). One skilled in the art will recognize that there are various ways to introduce the vicinal diol in a non-racemic fashion. In a preferred embodiment, a Sharpless Catalytic Asymmetric Dihydroxylation reaction is used. The Sharpless Catalytic Asymmetric Dihydroxylation reaction is known in the art and permits the transformation of an olefin to a vicinal diol in a predictable, non-racemic fashion with the requisite disposition for further elaboration. For example, this reaction may be carried out by combining an olefin, a chiral ligand, an organic solvent, water, an osmium catalyst and an oxidant under suitable reaction conditions to form a diol in a stereoselective manner. The chiral ligand, osmium catalyst, and oxidant used in this reaction may be obtained commercially as a mixture. In a preferred embodiment, AD-mix-α, containing a dihydroquinidine ligand or AD-mix-β containing a dihydroquinine ligand, supplied by Sigma-Aldrich, located in St. Louis Mo. is used. One skilled in the art will recognize that other chiral ligands may be used and the choice will depend upon the desired enantioselectivity. Examples of other suitable reaction conditions for carrying out the Sharpless Catalytic Asymmetric reaction are described for example, in PCT patent application publication number WO 91/16322, and the article by Kolb et al., *Catalytic Asymmetric Dihydroxylation*, Chem. Rev. 94, p. 2483–2547 (1994). The disclosures of these documents are incorporated herein by reference in their entireties.

The optically active butane diol of (IB) may then optionally be further reacted with an appropriate leaving group reagent or oxygen protecting group reagent to replace or protect the primary —OH of the butane diol to form the benzene compound of formula (I) where R may be H or an oxygen protecting group, or the moiety "OR" may be a leaving group.

The optically active benzene compound of formula (I) is then further reacted in the following manner to form the 2-hydroxymethyl chroman of formula (II). Prior to the cyclization reaction, discussed in further detail below, the —OR⁰ moiety of the benzene compound must be deprotected according to conventional techniques to form —OH, if R⁰ was not H. Following deprotection, the resulting phenol of formula IA:

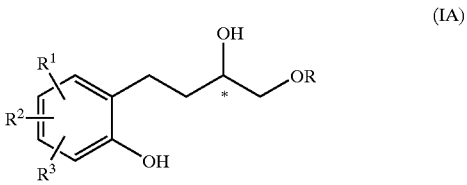

(IA)

is reacted in one or more reactions to form the optically active 2-hydroxymethyl-chroman of formula (II), where at least one of the reactions is a stereospecific cyclization reaction. Thus, through the stereospecific cyclization reaction, the asymmetry (e.g., % enantiomer excess) established in the dihydroxylation step is preserved in the 2-hydroxymethyl-chroman product. Preferably, the process of the present invention will provide a 2-hydroxymethyl-chroman of formula II having an enantiomer excess of at least about 30%, more preferably at least about 40%, and most preferably at least about 50%.

One skilled in the art will recognize that there are various ways to carry out the stereospecific cyclization reaction starting with the phenol of formula (IA). For example, if R is an oxygen protecting group or —OR is a leaving group, the cyclization may be carried out using a stereospecific intramolecular dehydration reaction, such as under Mitsunobu reaction conditions. If R is H, cyclization may be carried out by first treating the phenol of formula (IA) with a hydrogen halide, such as hydrogen bromide and a carboxylic acid such as acetic acid, and cyclizing the resulting compound with a base.

One preferred embodiment of a cyclization reaction scheme is illustrated in Scheme II, which is presented below. The result is a compound of formula II in which R is H.

SCHEME II

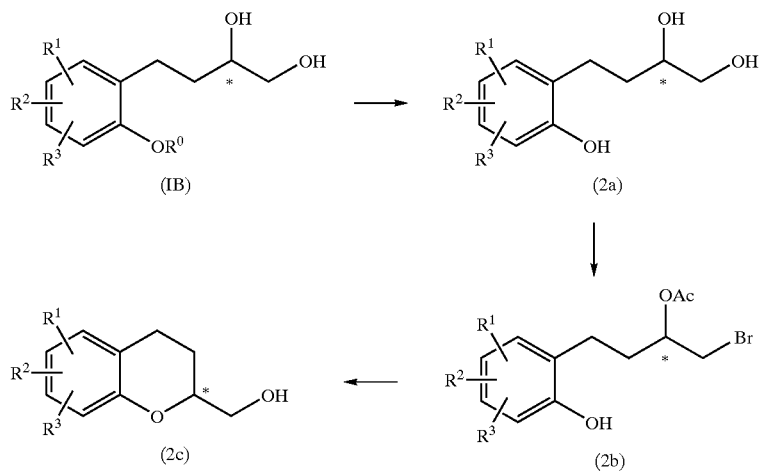

In the embodiment shown in Scheme II, if $R^0$ of formula (IB) is an oxygen protecting group, the $OR^0$ is deprotected using conventional techniques. For example, if $R^0$ is benzyl, deprotection may be carried out by hydrogenolysis with 10 wt. % palladium on activated carbon to form the triol of formula (2a). The triol may then be treated with a solution of 30% hydrogen bromide in acetic acid to provide a regioisomeric mixture of acetoxy bromides favoring the formation of the primary bromide of formula (2b). Cyclization of the bromide compound of formula (2b) to give the 2-hydroxymethyl-chroman may be carried out in the presence of a suitable base that is preferably an inorganic base such as an alkali metal or alkaline earth metal hydroxide or carbonate such as potassium or sodium hydroxide or potassium carbonate. The reaction may be conducted in any suitable solvent that is preferably polar such as an acoholic solvent (methanol or ethanol), dimethylformamide or tetrahydrofuran. In a preferred embodiment, the cyclization reaction is carried out with aqueous sodium hydroxide in methanol at 0° C. The resulting 2-hydroxymethyl-chroman (2c) is composed of a mixture of enantiomers that reflects the original stereoselectivity of the dihydroxylation reaction used to form the butanediol compound of formula (IB).

Another embodiment of a cyclization reaction scheme is illustrated in Scheme III below.

SCHEME III

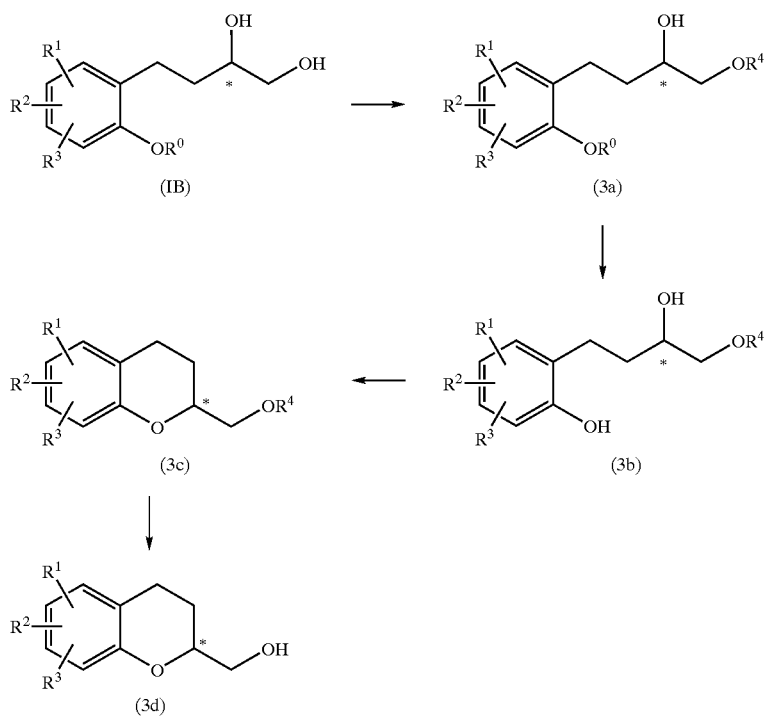

In this embodiment, the 2-hydroxymethyl-chroman compound of formula II may be prepared via chemoselective protection of the vicinal diol with a suitable oxygen protecting group or leaving group. For example, the butanediol compound of formula (IB), where $R^0$ is an oxygen protecting group, is treated with any oxygen protecting group reagent or leaving group reagent under reaction conditions known to those skilled in the art to form the compound of formula (3a), with $R^4$ being an oxygen protecting group or $OR^4$ being a leaving group. The $OR^0$ is then deprotected using conventional techniques. For example, if $R^0$ is benzyl, deprotection may be carried out by hydrogenolysis with 10 wt. % palladium on activated carbon to form the phenol of formula (3b). The phenol of formula (3b) is then subjected to a stereospecific intramolecular dehydration reaction to provide the optically active 2-hydroxymethyl-chroman of (3c). In a preferred embodiment, the dehydration reaction is performed under Mitsunobu reaction conditions, such as for example, in the presence of triphenylphosphine and diethylazodicarboxylate. One skilled in the art will recognize other suitable reaction conditions for performing this stereospecific dehydration reaction. For example, the articles by Mitsunobu, *The Use of Diethyl Azocicarboxylate and Triphenylphosphine in Synthesis and Transformation of Natural Products*, Synthesis, pages 1 to 28, (1981); and J. Dodge, et al., *Advances In The Mitsunobu Reaction For The Stereochemical Inversion Of Hindered Secondary Alcohols*, Recent Research Developments in Organic Chemistry (1) p. 273–283 (1997) provide many other suitable reaction conditions. The disclosure of these two articles is hereby incorporated by reference in their entireties.

In the last step, the compound of formula (3c) may optionally be converted under reaction conditions known to those skilled in the art to obtain a compound of formula (II) in which R is H. It is also possible to omit the last step, to obtain a compound of formula (II) in which R is an oxygen protecting group or "OR" is a leaving group.

Scheme IV, below, illustrates an embodiment of the type illustrated in Scheme III where $R^4$ is tosylate; the product is a compound of formula (II) in which R is tosylate. In a preferred embodiment, the butanediol is mono-tosylated by treatment with p-toluenesulfonyl chloride in a reaction solvent such as pyridine. The remaining reaction steps are carried out as described in Scheme (III).

One skilled in the art, in reading the above, will readily recognize that where catalysts or solvents are included in a reaction step of the process of the present invention, it is expected that other catalysts or solvents known in the art, but not mentioned herein, may be used. Moreover, those skilled in the art will recognize that the reactions disclosed herein can be performed under a variety of reaction conditions using the teachings herein in combination with the knowledge available to those skilled in the art. For example, various reaction temperatures, pressures, solvents, catalysts and equipment can be used in accordance with the process of the present invention. It is also contemplated for example, that although the processes described in the examples are batch, they could be adapted to for semi-continuous or continuous operations.

As described above, use of the process according to the invention permits the stereoselective synthesis of 2-hydroxymethyl-chromans. The ease of the reaction sequence, as well as the availability of the starting salicylaldehydes, makes this process a practical method for the preparation of optically active 2-hydroxymethyl-chromans. Benefits of using the process of the present invention over previously disclosed preparations include: 1) an efficient route to the general synthesis of 2-hydroxymethyl-chromans used in the preparation of 2-aminomethyl- and 2-azaheterocyclylmethyl-chromans which are used in the treatment of diseases of the central nervous system; 2) a process for the production of a single enantiomer without resolution and/or purification steps.

As previously mentioned, the 2-hydroxymethyl-chromans can be further reacted to prepare a variety of useful medicinal agents. For example, the 2-hydroxymethyl-chromans can be further reacted to form 2-aminomethyl- or 2-azaheterocyclylmethyl-chroman compounds, which are useful in the treatment of diseases of the central nervous system. Methods to synthesize these chromans are disclosed in for example U.S. Pat. Nos. 5,371,094, 5,318,988, and the Ellis "Chromenes, Chromenones and Chromones" article previously mentioned herein, the disclosures of which are hereby incorporated by reference in their entireties.

The following non-limiting examples describe and illustrate methods for carrying out the process of the present invention, as well as other aspects of the invention, and the results achieved thereby. Both an explanation of, and the actual procedures for, the various aspects of the present invention are described where appropriate. These examples are intended to be merely illustrative of the present invention and are not intended to limit the invention to the disclosed

SCHEME IV

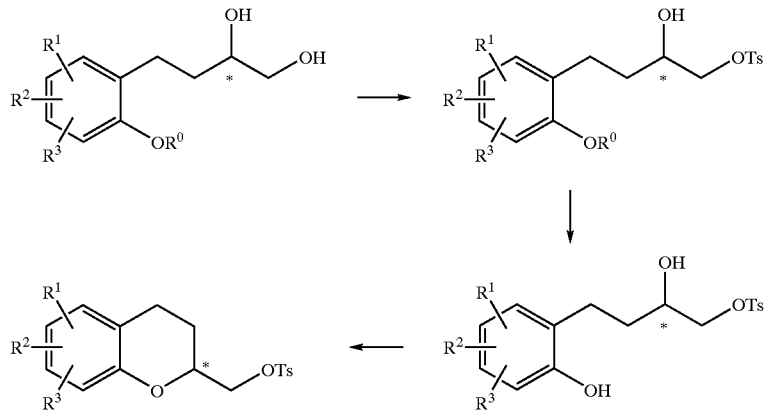

compounds and procedures. Variations and changes which are obvious to one skilled in the art are intended to be within the scope and nature of this invention.

EXAMPLE 1

Step 1: 2-(benzyloxy)-1-(3-butenyl)-3-methoxybenzene

To a solution of [2-(benzyloxy)-3-methoxyphenyl] methanol (14.82 g, 60.7 mmol) in dichloromethane (500 mL) at 0° C. is added carbon tetrabromide (26.16 g, 78.9 mmol) followed by portionwise addition of triphenyl phosphine (19.09 g, 72.8 mmol) and the reaction mixture is allowed to stir for 15 min. The reaction is quenched by the addition of water (500 mL) and extracted with dichloromethane (400 mL). The combined organic layers are washed with water (400 mL), aqueous sodium chloride (500 mL), dried (magnesium sulfate) and the solvent is removed in vacuo to give a crude solid. Purification by flash column chromatography (silica, ethyl acetate:hexanes 1:9) provides 18.46 g of a colorless oil which is dissolved in tetrahydrofuran (500 mL). The solution is cooled to 0° C. and allyl magnesiumbromide (1.0 M in diethyl ether, 121.4 mL, 121.4 mmol) is added dropwise and the reaction mixture is allowed to stir for 12 hours at room temperature. The reaction is quenched by the addition of aqueous ammonium chloride (200 mL) and water (300 mL) and extracted with diethyl ether (3×250 mL). The combined organic layers extracts are washed with water (400 mL), aqueous sodium chloride (500 mL), dried (magnesium sulfate) and the solvent is removed in vacuo to give an oil. Purification by flash column chromatography (silica, ethyl acetate:hexanes 1:20) provides 13.84 g (85%) of 2-(benzyloxy)-1-(3-butenyl)-3-methoxybenzene as a colorless oil. $R_f$=0.62 (silica, ethyl acetate:hexanes 3:2); Anal. Calcd. for $C_{18}H_{20}O_2 \cdot 0.25H_2O$: C, 79.23; H, 7.57. Found: C, 79.02; H, 7.47.

Step 2: (2S)-4-[2-(benzyloxy)-3-methoxyphenyl]-1,2-butanediol

To a suspension of AD-mix-α (63.28 g) in water:tert-butyl alcohol (1:1, 300 mL) cooled to 0° C. is slowly added via an addition funnel to a solution of 2-(benzyloxy)-1-(3-butenyl)-3-methoxybenzene (12.13 g, 45.2 mmol) in water:tert-butyl alcohol (1:1, 300 mL). The reaction mixture is allowed to stir at room temperature for 12 h. The reaction mixture is quenched by the addition of sodium sulfite. The reaction mixture is diluted with water (500 mL) and ethyl acetate (500 mL). The aqueous phase is separated and extracted with ethyl acetate (2×200 mL). The combined organic extracts are washed with aqueous sodium chloride (400 mL), dried (magnesium sulfate) and the solvent is removed in vacuo to give a crude oil. Purification by flash column chromatography (silica, ethyl acetate:hexanes 4:1) provides 12.57 g (92%, 40% ee) of (2S)-4-[2-(benzyloxy)-3-methoxyphenyl]-1,2-butanediol as a colorless oil. $[\alpha]_D^{25}$=−3.04 (c 10.2 in methanol, 40% ee); $R_f$=0.72 (silica, ethyl acetate:hexanes 4:1); Anal. Calcd. for $C_{18}H_{22}O_4 \cdot 0.1H_2O$: C, 71.08; H, 7.36. Found: C, 70.95; H, 7.33.

Step 3: 2-((3S)-4-{[tert-butyl(dimethyl)silyl]oxy}-3-hydroxybutyl)-6-methoxyphenol To a solution of (2S)-4-[2-(benzyloxy)-3-methoxyphenyl]-1,2-butanediol (8.00 g, 26.5 mmol) in N,N-dimethylformamide (250 mL) cooled to 0° C. is added tert-butyldimethylsilyl chloride (4.39 g, 29.1 mmol) followed by imidazole (2.16 g, 31.8 mmol) and the reaction mixture is allowed to stir at room temperature for 4 h. The reaction mixture is diluted with water (500 mL) and ethyl acetate (200 mL). The aqueous phase is separated and extracted with ethyl acetate (2×100 mL). The combined organic extracts are washed with aqueous hydrogen chloride (200 mL), water (4×200 mL), aqueous sodium chloride (300 mL), dried (magnesium sulfate) and the solvent is removed in vacuo to give a crude oil. The residue is dissolved in ethanol (300 mL), palladium on carbon (10 wt. %, 1.00 g) is added, and the reaction mixture is shaken under an $H_2$ atmosphere (50 psi) for 6 h. The reaction mixture is filtered (celite) and the solvent removed in vacuo to provide a crude oil. Purification by flash column chromatography (silica, ethyl acetate:hexanes 1:4) provides 7.33 g (85%, 40% ee) of 2-((3S)-4-{[tert-butyl(dimethyl)sily]oxy}-3-hydroxybutyl)-6-methoxyphenol as a colorless oil which crystallized upon standing. $R_f$=0.53 (silica, ethyl acetate:hexanes 1:4); mp 44–46° C.; Anal. Calcd. for $C_{17}H_{30}O_4Si$: C, 62.54; H, 9.26. Found: C, 62.41; H, 9.19.

Step 4: tert-butyl(dimethyl)silyl [(2R)-8-methoxy-3,4-dihydro-2H-chromen-2-yl]methyl ether To a solution of 2-((3S)-4-{[tert-butyl(dimethyl)silyl]oxy}-3-hydroxybutyl)-6-methoxyphenol (6.90 g, 21.1 mmol) in toluene (250 mL) cooled to 0° C. is added triphenylphosphine (6.10 g, 23.2 mmol) followed by dropwise addition of diethyl azodicarboxylate (4.05 g, 23.2 mmol). The reaction mixture is allowed to stir at room temperature for 15 min. The reaction-mixture is quenched by the addition of water (300 mL). The aqueous layer is separated and extracted with diethyl ether (2×150 mL). The combined organic extracts are washed with water (200 mL), aqueous sodium chloride (300 mL), dried (magnesium sulfate) and the solvent is removed in vacuo to give a crude oil. Purification by flash column chromatography (silica, ethyl acetate:hexanes 1:4) provided 4.94 g (76%, 40% ee) of tert-butyl(dimethyl)silyl [(2R)-8-methoxy-3,4-dihydro-2H-chromen-2-yl]methyl ether as a colorless oil. $[\alpha]_D^{25}$=−25.84 (c 10.82 in chloroform, 40% ee); $R_f$=0.68 (silica, ethyl acetate:hexanes 1:4); Anal. Calcd. for $C_{17}H_{28}O_3Si \cdot 0.1H_2O$: C, 65.8; H, 9.16. Found: C, 65.75; H, 8.88.

EXAMPLE 2

[(2R)-8-methoxy-3,4-dihydro-2H-chromen-2-yl]methanol

Method A: from (2S)-4-[2-(benzyloxy)-3-methoxyphenyl]-1,2-butanediol

To a solution of (2S)-4-[2-(benzyloxy)-3-methoxyphenyl]-1,2-butanediol (12.00 g, 39.7 mmol) in ethanol (400 mL) is added palladium on carbon (10 wt. %, 1.2 g) and the reaction mixture is shaken under an $H_2$ atmosphere (50 psi) for 12 h. The reaction mixture is filtered (celite) and the solvent removed in vacuo to provide a crude oil. The residue is dissolved in hydrogen bromide (30 wt. % in acetic acid, 200 mL) and the reaction mixture is stirred at 0° C. for 2 h. The reaction mixture is quenched by the addition of water (500 mL) and extracted with ethyl acetate (3×200 mL). The combined organic extracts are washed with water (3×200 mL), aqueous sodium chloride (300 mL), dried (magnesium sulfate), and the solvent is removed in vacuo to provide a crude oil. The residue is dissolved in methanol (100 mL) and the resulting solution is slowly added to a solution of aqueous sodium hydroxide (2.5 M, 150 mL) in water (350 mL) and the reaction mixture is allowed to stir at 0° C. for 30 min. The reaction mixture is quenched by the addition of aqueous hydrogen chloride (1.0 M, 500 mL) and extracted with ethyl acetate (3×200 mL). The combined organic extracts are washed with water (2×200 mL), aqueous sodium chloride (300 mL), dried (magnesium sulfate), and the solvent is removed in vacuo to provide a crude oil. Purification by flash column chromatography (silica, ethyl acetate:hexanes 1:1) provides 5.38 g (70%, 40% ee) of [(2R)-8-methoxy-3,4-dihydro-2H-chromen-2-yl]methanol as a white crystalline solid. $[\alpha]_D^{25}$=−60.51 (c 9.62 in chloroform, 40% ee); $R_f$=0.52 (silica, ethyl acetate:hexanes 1:1); mp 65–69° C.; Anal. Calcd. for $C_{11}H_{14}O_3$: C, 68.02; H, 7.27. Found: C, 67.92; H, 7.30.

Method B: from tert-butyl(dimethyl)silyl [(2R)-8-methoxy-3,4-dihydro-2H-chromen-2-yl]methyl ether.

To a solution of tert-butyl(dimethyl)silyl [(2R)-8-methoxy-3,4-dihydro-2H-chromen-2-yl]methyl ether (4.50 g, 14.6 mmol) in tetrahydrofuran (150 mL) at 0° C. is added excess tetrabutylammonium fluoride (1.0 M in tetrahydrofuran) and the reaction mixture is allowed to stir at 22° C. for 30 min. The solvent is removed in vacuo and the residue is purified by flash column chromatography (silica, ethyl acetate:hexanes 1:1) to give 2.49 g (88%, 40% ee) of [(2R)-8-methoxy-3,4-dihydro-2H-chromen-2-yl]methanol as a white crystalline solid.

EXAMPLE 3
[(2R)-8-methoxy-3,4-dihydro-2H-chromen-2-yl]methyl 4-methylbenzenesulfonate To a solution of [(2R)-8-methoxy-3,4-dihydro-2H-chromen-2-yl]methanol (5.00 g, 25.7 mmol) in dichloromethane (250 mL) is added p-toluenesulfonyl chloride (9.82 g, 51.5 mmol), 4-(dimethylamino)pyridine (0.62 g, 5.15 mmol), and N,N-diisopropylethylamine (8.32 g, 64.4 mmol) and the reaction mixture is heated to 50° C. for 12 h. The reaction mixture is quenched by the addition of water (500 mL). The aqueous layer is separated and extracted with dichloromethane (200 mL). The combined organic extracts are washed with aqueous hydrogen chloride (1.0 M, 200 mL), water (200 mL), aqueous sodium chloride (200 mL), dried (magnesium sulfate), and the solvent is removed in vacuo to provide a crude solid. Purification by flash column chromatography (silica, ethyl acetate:hexanes 2:3) provides 6.45 g (72%, 40% ee) of [(2R)-8-methoxy-3,4-dihydro-2H-chromen-2-yl]methyl 4-methylbenzenesulfonate as a white crystalline solid. $[\alpha]_D^{25}$=−20.30 (c 13.1 in chloroform, 40% ee); $R_f$=0.71 (silica, ethyl acetate:hexanes 2:3); mp 115–117° C.; Anal. Calcd. for $C_{18}H_{20}O_5S$: C, 62.05; H, 5.79. Found: C, 61.99; H, 5.81.

EXAMPLE 4
Step 1: [1-(benzyloxy)-2-naphthyl]methanol

To a solution of 1-(benzyloxy)-2-naphthaldehyde (7.00 g, 26.7 mmol) in methanol (250 mL) at 0° C. is added sodium borohydride (1.51 g, 40.0 mmol) and the reaction mixture is allowed to stir at room temperature for 24 h. The solvent is removed in vacuo to give a crude solid which is partitioned between ethyl acetate (300 mL) and water (300 mL). The organic layer is separated and washed with water (300 mL), aqueous sodium chloride (300 mL), dried (magnesium sulfate) and filtered through a plug of silica (10 cm×5 cm). The solvent is removed in vacuo to give 6.98 g (99%) of [1-(benzyloxy)-2-naphthyl]methanol as white crystalline solid. $R_f$=0.36 (silica, dichloromethane:hexanes 3:2); mp 85–87° C. Anal. Calcd. for $C_{18}H_{16}O_2$: C, 81.24; H, 6.14. Found: C, 81.03; H, 5.98.

Step 2: (2S)-4-[1-(benzyloxy)-2-naphthyl]-1,2-butanediol

To a solution of [1-(benzyloxy)-2-naphthyl]methanol (7.22 g, 27.3 mmol) in dichloromethane (300 mL) at 0° C. is added carbon tetrabromide (9.95 g, 30.0 mmol) followed by portionwise addition of triphenyl phosphine (7.52 g, 28.7 mmol) and the reaction mixture is allowed to stir for 15 min. The reaction is quenched by the addition of water (300 mL) and extracted with dichloromethane (200 mL). The combined organic layers are washed with water (200 mL), aqueous sodium chloride (200 mL), dried (magnesium sulfate) and the solvent is removed in vacuo to give a crude solid. Purification by flash column chromatography (silica, ethyl acetate:hexanes 1:9) provides 8.57 g (96%) of a colorless oil which is dissolved in tetrahydrofuran (300 mL). The solution is cooled to 0° C. and allyl magnesiumbromide (1.0 M in diethyl ether, 39.3 mL, 39.3 mmol) is added dropwise and the reaction mixture is allowed to stir for 12 h at room temperature. The reaction is quenched by the addition of aqueous ammonium chloride (100 mL) and water (200 mL) and extracted with diethyl ether (2×150 mL). The combined organic layers extracts are washed with water (400 mL), aqueous sodium chloride (200 mL), dried (magnesium sulfate) and the solvent is removed in vacuo to give an oil. Purification by flash column chromatography (silica, ethyl acetate:hexanes 1:20) provides 5.74 g (76%) of a colorless oil which is dissolved in water:tert-butyl alcohol (1:1, 100 mL) and added via an addition funnel to a suspension of AD-mix-α (27.87 g) in water:tert-butyl alcohol (1:1, 200 mL) and the reaction mixture is allowed to stir at 0° C. for 12 h. The reaction mixture is quenched by the addition of sodium sulfite. The reaction mixture is diluted with water (300 mL) and ethyl acetate (200 mL). The aqueous phase is separated and extracted with ethyl acetate (2×150 mL). The combined organic extracts are washed with aqueous sodium chloride (250 mL), dried (magnesium sulfate) and the solvent is removed in vacuo to give a crude oil. Purification by flash column chromatography (silica, ethyl acetate:hexanes 4:1) provides 5.39 g (84%, 50% ee) of (2S)-4-[1-(benzyloxy)-2-naphthyl]-1,2-butanediol as a colorless oil. $[\alpha]_D^{25}$=−3.94 (c 19.31 in methanol, 50% ee); $R_f$=0.56 (silica, ethyl acetate:hexanes 4:1); Anal. Calcd. for $C_{21}H_{22}O_3.0.25\ CH_3CO_2C_2H_5$ C, 76.72; H, 7.02. Found: C, 76.31; H, 7.00.

Step 3: (2S)-4-(1-hydroxy-2-naphthyl)-1,2-butanediol

To a solution of (2S)-4-[1-(benzyloxy)-2-naphthyl]-1,2-butanediol (5.63 g, 17.5 mmol) in ethanol (150 mL), palladium on carbon (10 wt. %, 0.56 g) is added, and the reaction mixture is shaken under an $H_2$ atmosphere (50 psi) for 6 h. The reaction mixture is filtered (celite) and the solvent removed in vacuo to provide a crude oil. Purification by flash column chromatography (silica, ethyl acetate:hexanes 4:1) provides 3.81 g (94%, 50% ee) of (2S)-4-(1-hydroxy-2-naphthyl)-1,2-butanediol as a colorless oil which crystallizes upon standing. $[\alpha]_D^{25}$=+11.93 (c 10.06 in chloroform, 50% ee); $R_f$=0.50 (silica, ethyl acetate:hexanes 4:1); mp 105–108° C.; Anal. Calcd. for $C_{14}H_{16}O_3$: C, 72.39; H, 6.94. Found: C, 72.20; H, 7.18.

Step 4: (2R)-3,4-dihydro-2H-benzo[h]chromen-2-ylmethanol (2S)-4-(1-hydroxy-2-naphthyl)-1,2-butanediol (3.50 g, 15.1 mmol) is dissolved in hydrogen bromide (30 wt. % in acetic acid, 100 mL) and the reaction mixture is stirred at 0° C. for 2 h. The reaction mixture is quenched by the addition of water (500 mL) and extracted with ethyl acetate (3×200 mL). The combined organic extracts are washed with water (3×200 mL), aqueous sodium chloride (300 mL), dried (magnesium sulfate), and the solvent is removed in vacuo to provide a crude oil. The residue is dissolved in methanol (100 mL) and the resulting solution is slowly added to a solution of aqueous sodium hydroxide (2.5 M, 150 mL) in water (350 mL) and the reaction mixture is allowed to stir at 0° C. for 30 min. The reaction mixture is quenched by the addition of aqueous hydrogen chloride (1.0 M, 500 mL) and extracted with ethyl acetate (3×200 mL). The combined organic extracts are washed with water (2×200 mL), aqueous sodium chloride (300 mL), dried (magnesium sulfate), and the solvent is removed in vacuo to provide a crude oil. Purification by flash column chromatography (silica, ethyl acetate:hexanes 1:1) provides 5.38 g (70%, 50% ee) of (2R)-3,4-dihydro-2H-benzo[h]chromen-2-ylmethanol as a colorless oil. $[\alpha]_D^{25}$=−51.23 (c 11.58 in chloroform, 50% ee); $R_f$=0.52 (silica, ethyl acetate:hexanes 1:1); Anal. Calcd. for $C_{14}H_{14}O_2.0.25H_2O$: C, 76.86; H, 6.68. Found: C, 76.47; H, 6.38.

EXAMPLE 5
(2R)-3,4-dihydro-2H-benzo[h]chromen-2-ylmethyl 4-methylbenzenesulfonate To a solution of (2R)-3,4-dihydro-2H-benzo[h]chromen-2-ylmethanol (0.90 g, 4.22 mmol) in dichloromethane (50 mL) is added p-toluenesulfonyl chloride (1.61 g, 8.44 mmol), 4-(dimethylamino)pyridine (0.10 g, 0.84 mmol), and N,N-diisopropylethylamine (1.20 g, 9.28 mmol) and the reaction mixture is heated to 50° C. for 12 h. The reaction mixture is quenched by the addition of water (100 mL). The aqueous layer is separated and extracted with dichloromethane (100 mL). The combined organic extracts are washed with aqueous hydrogen chloride (1.0 M, 100 mL), water (100 mL), aqueous sodium chloride (100 mL), dried (magnesium sulfate), and the solvent is removed in vacuo to provide a crude solid. Purification by flash column chromatography (silica, ethyl acetate:hexanes 2:3) provides 1.20 g (77%, 50% ee) of (2R)-3,4-dihydro-2H-benzo[h]chromen-2-ylmethyl 4-methylbenzenesulfonate as a white solid. $[\alpha]_D^{25}=-10.23$ (c 10.16 in chloroform, 50% ee); $R_f$=0.68 (silica, ethyl acetate:hexanes 2:3); mp 107–111° C.; Anal. Calcd. for $C_{21}H_{20}O_4S$: C, 68.46; H, 5.47. Found: C, 68.10; H, 5.27.

EXAMPLE 6
Step 1: 6-allyl-5-(benzyloxy)quinoline
Treatment of 6-allylquinolin-5-ol with potassium carbonate and benzyl bromide in N,N-dimethylformamide followed by aqueous work-up and extraction with ethyl acetate provides 6-allyl-5-(benzyloxy)quinoline.

Step 2: 5-(benzyloxy)-6-[(1E)-prop-1-enyl]quinoline
Treatment of a refluxing solution of 6-allyl-5-(benzyloxy)quinoline in dichloromethane with bis(acetonitrile)dichloropalladium (II) followed by removal of the solvent and subsequent purification by flash column chromatography provides 5-(benzyloxy)-6-[(1E)-prop-1-enyl]quinoline.

Step 3: 5-(benzyloxy)quinoline-6-carbaldehyde
Treatment of 5-(benzyloxy)-6-[(1E)-prop-1-enyl]quinoline in methylene chloride with excess ozone at –78° C. followed by addition of diisopropylethylamine, aqueous work-up, and subsequent purification by flash column chromatography provides 5-(benzyloxy)quinoline-6-carbaldehyde.

Step 4: [5-(benzyloxy)quinolin-6-yl]methanol
Treatment of 5-(benzyloxy)quinoline-6-carbaldehyde with sodium borohydride in methanol following the procedure described for Example 4, step 1 provides [5-(benzyloxy)quinolin-6-yl]methanol.

Step 5: 5-(benzyloxy)-6-but-3-enylquinoline
Treatment of [5-(benzyloxy)quinolin-6-yl]methanol with carbontetrabromide and triphenylphosphine in dichloromethane and subsequent treatment with allyl magnesiumbromide in tetrahydrofu ran following the procedure described for Example 1, step 1 provides 5-(benzyloxy)-6-but-3-enylquinoline.

Step 6: (2S)-4-[5-(benzyloxy)quinolin-6-yl]butane-1,2-diol
Addition of 5-(benzyloxy)-6-but-3-enylquinoline to a suspension of AD-mix-α in water:tert-butyl alcohol following the procedure described for Example 1, step 2 gives (2S)-4-[5-(benzyloxy)quinolin-6-yl]butane-1,2-diol.

Step 7: (2S)-4-[5-(benzyloxy)quinolin-6-yl]-2-hydroxybutyl 4-methylbenzene Sulfonate
Treatment of (2S)-4-[5-(benzyloxy)quinolin-6-yl]butane-1,2-diol with p-toluenesulfonyl chloride in pyridine followed by aqueous work-up, extraction with ethyl acetate and subsequent purification by flash column chromatography provides (2S)-4-[5-(benzyloxy)quinolin-6-yl]-2-hydroxybutyl 4-methylbenzene sulfonate.

Step 8: (2S)-2-hydroxy-4-(5-hydroxyquinolin-6-yl)butyl 4-methylbenzenesulfonate
Treatment of (2S)-4-[5-(benzyloxy)quinolin-6-yl]-2-hydroxybutyl 4-methylbenzene sulfonate with palladium on carbon (10 wt. %) in ethanol following the procedure described in Example 9 provides (2S)-2-hydroxy-4-(5-hydroxy-quinolin-6-yl)butyl 4-methylbenzenesulfonate.

Step 9: (2R)-3,4-dihydro-2H-pyrano[2,3-f]quinolin-2-ylmethyl 4-methylbenzenesulfonate
Treatment of (2S)-2-hydroxy-4-(5-hydroxyquinolin-6-yl)butyl 4-methylbenzene sulfonate with triphenylphosphine and diethyl azodicarboxylate in toluene following the procedure of Example 4 provides (2R)-3,4-dihydro-2H-pyrano[2,3-f]quinolin-2-ylmethyl 4-methyl-benzenesulfonate.

What is claimed is:

1. A process for the stereoselective synthesis of a 2-hydroxymethyl-chroman comprising (a) providing an optically active benzene compound of formula (I),

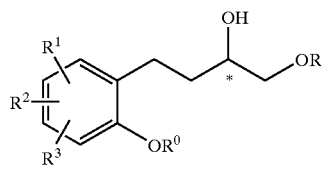

wherein

R⁰ is hydrogen or an oxygen protecting group,

R is an oxygen protecting group or hydrogen, or the moiety OR is a leaving group, and $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$ alkoxy group, a $C_2$ to $C_7$ alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii) or iii);

(b) if R⁰ is not H, deprotecting the OR⁰ moiety of formula (I) to produce a phenol compound of formula (IA)

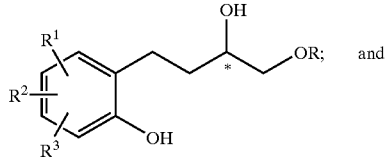
(IA)

(c) reacting the phenol of formula (IA) in one or more reactions to form a 2-hydroxymethyl-chroman of formula (II)

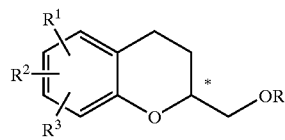
(II)

wherein at least one of the reactions is a stereospecific cyclization reaction.

2. The process of claim 1 wherein R of formula (I) and (IA) is hydrogen;

wherein prior to the stereospecific cyclization reaction, the phenol of formula (IA) is treated with hydrogen bromide and acetic acid to produce a bromine compound of formula (2b)

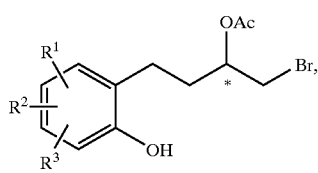
(2b)

where Ac is an acyl group; and wherein the stereospecific cyclization reaction comprises treating the bromine compound of formula (2b) with a base.

3. The process of claim 1 wherein the R of formula (I) and (IA) is an oxygen protecting group or the moiety OR of formula (I) and (IA) is a leaving group, and wherein the stereospecific cyclization reaction comprises treating the phenol of formula (IA) with triphenylphosphine and diethyl azodicarboxylate to produce the compound of formula (II).

4. The process of claim 3 wherein OR is tosylate.

5. The process of claim 1 wherein the compound of formula (I) is formed by one or more reactions comprising an osmium-catalyzed asymmetric dihydroxylation of a butene compound of formula (1e)

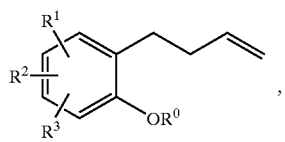
(1e)

to produce a compound of formula (IB)

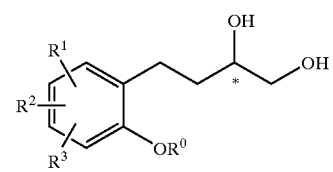
(IB)

wherein $R^0$, $R^1$, $R^2$ and $R^3$ are defined as in claim 1.

6. The process of claim 5, wherein prior to deprotecting the $OR^0$ moiety of formula (I), the compound of formula (IB) is treated with a leaving group reagent or oxygen-protecting group reagent to form a compound of formula (3a)

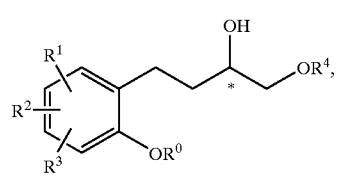
(3a)

wherein $R^4$ is an oxygen protecting group or the moiety $OR^4$ is a leaving group.

7. The process of claim 5 wherein the butene compound of formula (1e) is formed in one or more reactions from a compound of formula (1b)

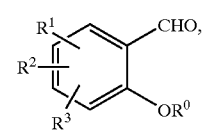
(1b)

wherein at least one of the reactions is an intermolecular allylation reaction.

8. The process of claim 1 wherein the benzene compound of formula (I) is provided having an enantiomer excess of at least about 30%.

9. The process of claim 1 wherein the 2-hydroxymethyl-chroman of formula (II) formed has an enantiomer excess of at least about 30%.

10. The process of claim 1 wherein the 2-hydroxymethyl-chroman of formula (II) is further reacted to form a 2-aminomethyl-chroman compound or an azaheterocyclyl-methylchroman compound.

11. A process for synthesizing a 2-hydroxymethyl-chroman comprising:

a) treating an optically active triol compound of formula (2a)

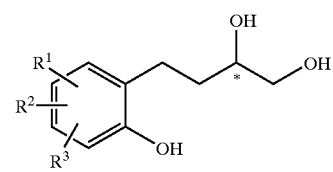
(2a)

with hydrogen bromide and acetic acid to form an optically active compound of formula (2b), where Ac is acyl

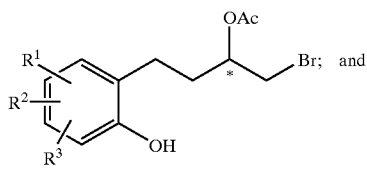

(2b)

b) treating the compound of (2b) with a base to stereospecifically produce an optically active compound of formula (2c)

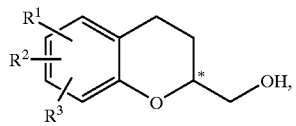

(2c)

wherein $R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$alkoxy group, a $C_2$ to $C_7$alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$ alkyl or alkoxy group, an amino group or a mono- or di-alkylamino having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii) or iii).

12. The process of claim 11 further comprising producing the triol compound of formula (2a) by a reaction comprising deprotecting a butanediol of formula (IB)

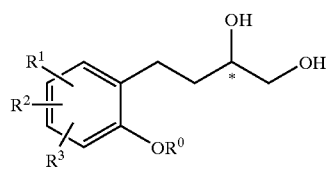

(IB)

to replace the $R^0$ with H;

wherein $R^0$ represents an oxygen protecting group and $R^1$, $R^2$ and $R^3$ are defined as in claim 11.

13. A process for synthesizing a 2-hydroxymethylchroman comprising:

a) deprotecting an optically active compound of formula (3a)

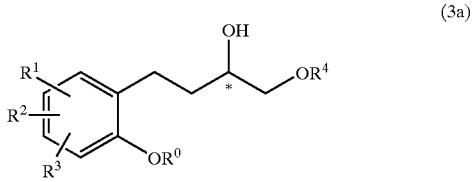

(3a)

to replace $R^0$ with H and produce a phenol compound of formula (3b)

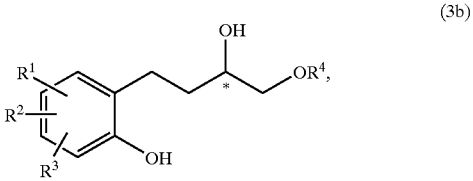

(3b)

wherein $R^0$ is an oxygen protecting group;

$R^4$ is an oxygen protecting group or the moiety $OR^4$ is a leaving group;

$R^1$, $R^2$ and $R^3$ are independently selected from hydrogen, a halogen atom, a cyano, azido, nitro, hydroxyl, carboxyl, acyl or carboxamido group, a $C_1$ to $C_6$ alkyl group, a 5- to 7-membered aromatic group optionally having as ring members up to 2 heteroatoms independently selected from O, N or S, a $C_5$ to $C_7$ membered aryloxy group, a $C_1$ to $C_6$alkoxy group, a $C_2$ to $C_7$alkenyl group, a carboalkoxy group having 1 to 6 carbon atoms in the alkyl chain, alkanamido group having 1 to 6 carbon atoms in the alkyl chain, alkanesulfonamido group having 1 to 6 carbon atoms in the alkyl chain, an alkanoyloxy group having 1 to 6 carbon atoms in the alkyl chain, a perhalogenated $C_1$ to $C_6$alkyl oralkoxy group, an amino group or a mono- or di-alkylamino having 1 to 6 carbon atoms per alkyl chain, or two of $R^1$, $R^2$ or $R^3$, taken together, form a 5- to 7-membered saturated, partly saturated, unsaturated, or aromatic carbocyclic or bridged carbocyclic ring, wherein the ring may i) optionally have up to two ring atoms selected from S, N, or O, ii) optionally have as a ring member up to 2 carbonyl groups or iii) optionally be substituted by 1 to 2 $R^5$ substituents where each $R^5$ substituent is independently selected from a halogen atom, a cyano, nitro or hydroxyl group, a $C_1$–$C_6$ alkyl group, a $C_1$–$C_6$ alkoxy group, a $C_3$–$C_6$ cycloalkyl group, a 5- to 7-membered aromatic group optionally having 1–2 ring atoms selected from N, O or S, or in spiro form a carbocyclic ring having 5 to 7 carbon atoms, or any combination of i), ii) or iii); and b) treating the phenol compound of formula (3b) with triphenylphosphine and diethyl azodicarboxylate to stereospecifically produce an optically active chroman compound of formula (3c)

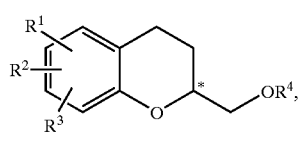 (3c)

wherein $R^1$, $R^2$, $R^3$ and $R^4$ are defined as in formula 3(b).

14. The process of claim 13 further comprising treating the chroman compound of formula (3c) to replace $R^4$ with H or $OR^4$ with OH.

15. The process of claim 13 further comprising forming the compound of formula (3a) by a reaction comprising treating a compound of formula (IB)

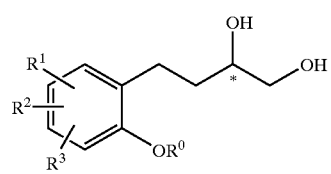 (IB)

with a leaving group reagent or oxygen-protecting group reagent, wherein $R^0$, $R^1$, $R^2$ and $R^3$ are defined as in claim 13.

16. The process of claim 13 wherein $OR^4$ is tosylate and the reagent is p-toluenesulfonyl chloride.

* * * * *